United States Patent
Ishii et al.

(10) Patent No.: US 9,974,495 B2
(45) Date of Patent: May 22, 2018

(54) X-RAY CT APPARATUS, IMAGE PROCESSING DEVICE, AND IMAGE RECONSTRUCTION METHOD

(71) Applicant: HITACHI, LTD., Tokyo (JP)

(72) Inventors: Sunao Ishii, Tokyo (JP); Takayuki Kadomura, Tokyo (JP)

(73) Assignee: HITACHI, LTD., Tokyo (JP)

( * ) Notice: Subject to any disclaimer, the term of this patent is extended or adjusted under 35 U.S.C. 154(b) by 185 days.

(21) Appl. No.: 15/104,090

(22) PCT Filed: Jan. 15, 2015

(86) PCT No.: PCT/JP2015/050900
§ 371 (c)(1),
(2) Date: Jun. 13, 2016

(87) PCT Pub. No.: WO2015/108097
PCT Pub. Date: Jul. 23, 2015

(65) Prior Publication Data
US 2016/0317102 A1    Nov. 3, 2016

(30) Foreign Application Priority Data
Jan. 20, 2014 (JP) .................................. 2014-007510

(51) Int. Cl.
*A61B 6/00* (2006.01)
*A61B 6/03* (2006.01)
*G06T 11/00* (2006.01)

(52) U.S. Cl.
CPC ............ *A61B 6/035* (2013.01); *A61B 6/032* (2013.01); *A61B 6/5205* (2013.01); *A61B 6/527* (2013.01);
(Continued)

(58) Field of Classification Search
None
See application file for complete search history.

(56) References Cited

U.S. PATENT DOCUMENTS

| | | | | |
|---|---|---|---|---|
| 2013/0101079 A1* | 4/2013 | Hough | ..................... | A61B 6/03 378/8 |
| 2013/0279644 A1* | 10/2013 | Yanagida | ............... | A61B 6/032 378/8 |
| 2014/0226887 A1 | 8/2014 | Takahashi et al. | | |

FOREIGN PATENT DOCUMENTS

| | | |
|---|---|---|
| JP | 2008-279153 | 11/2008 |
| JP | 2013-172889 | 9/2013 |
| WO | WO 2012/147471 A1 | 11/2012 |

OTHER PUBLICATIONS

International Search Report in PCT/JP2015/050900.

* cited by examiner

*Primary Examiner* — Hoon Song
(74) *Attorney, Agent, or Firm* — Cooper & Dunham LLP

(57) ABSTRACT

An X-ray CT apparatus 1 stores an image quality improvement table 3 indicating levels of image quality improvement effects for a plurality of image quality improvement processes in a storage device 123. In a case where imaging is performed while modulating an X-ray irradiation amount on the basis of predetermined dose modulation data, an image processing device 122 acquires a reference dose used as a reference of image quality, and acquires an irradiation X-ray dose during imaging for image reconstruction target projection data from the dose modulation data. The image processing device 122 determines an image quality improvement process for obtaining image quality used as a reference by referring to the image quality improvement table 3 on the basis of a ratio between the dose values, and performs the determined image quality improvement process on the reconstruction target projection data.

9 Claims, 15 Drawing Sheets

3  IMAGE QUALITY IMPROVEMENT TABLE

| IMAGE QUALITY IMPROVEMENT PROCESS | EFFECT |
|---|---|
| Level 1 | +30% |
| Level 2 | +40% |
| Level 3 | +50% |
| Level 4 | +60% |
| Level 5 | +70% |

(52) U.S. Cl.
CPC ............ *A61B 6/5258* (2013.01); *A61B 6/541* (2013.01); *A61B 6/542* (2013.01); *G06T 11/005* (2013.01); *G06T 11/008* (2013.01); *A61B 6/461* (2013.01); *A61B 6/465* (2013.01)

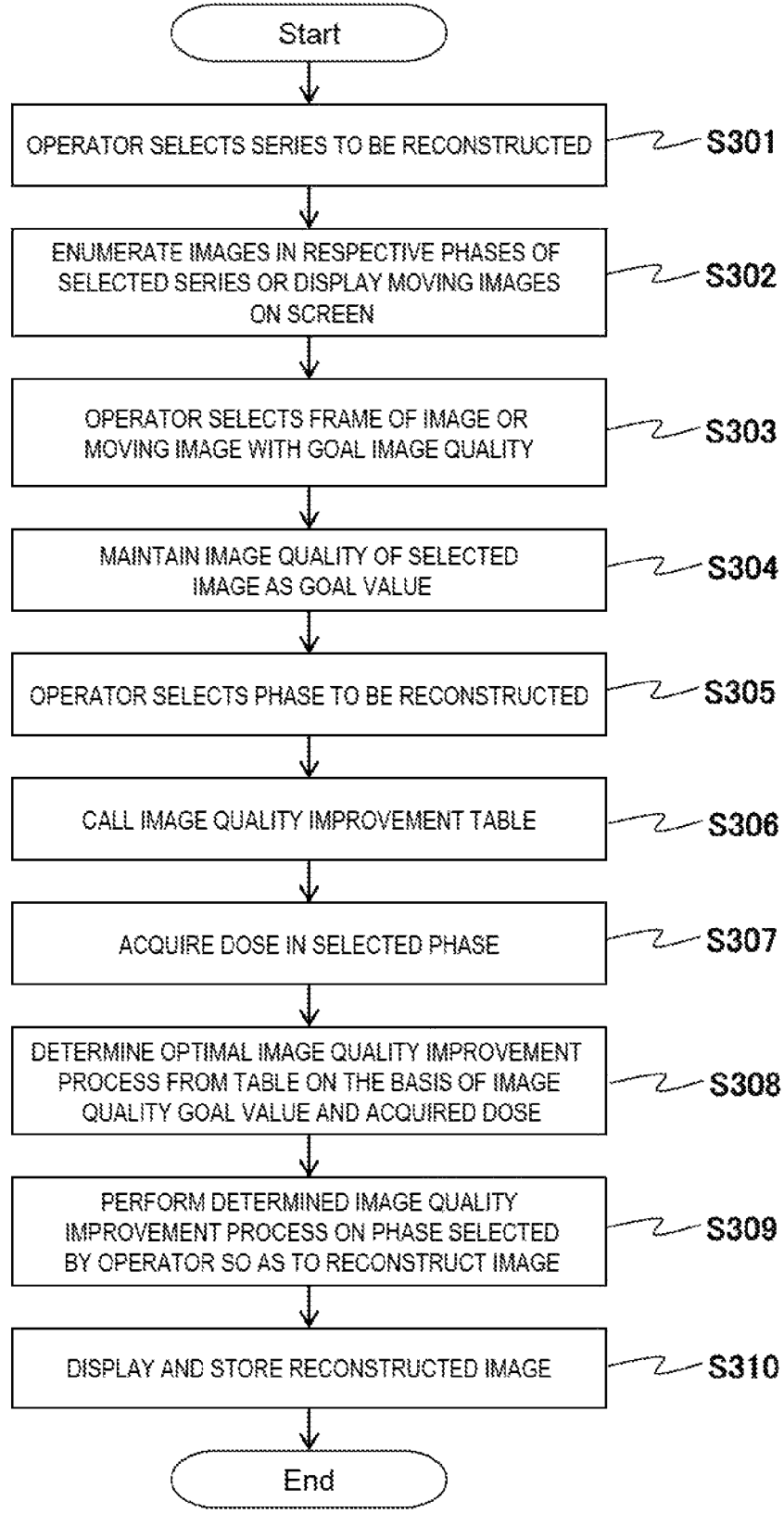

X-RAY CT APPARATUS, IMAGE PROCESSING DEVICE, AND IMAGE RECONSTRUCTION METHOD

TECHNICAL FIELD

The present invention relates to an X-ray CT apparatus, an image processing device, and an image reconstruction method, and particularly to an image reconstruction process using projection data obtained through imaging by modulating an irradiation X-ray dose.

BACKGROUND ART

In the related art, in a case where a part in motion is imaged by an X-ray computed tomography (CT) apparatus, artifacts are caused in an obtained tomographic image due to the motion. In order to reduce the artifacts, generally, measurement is performed in accordance with physiological activity by using a biosensor such as an electrocardiograph or a respiration sensor, and imaging is controlled or an image is processed by using an obtained measurement signal. For example, in imaging targeting the heart, an electrocardiographic synchronous reconstruction method is performed in which projection data with a phase in which motion is reduced is collected on the basis of electrocardiographic information measured by using an electrocardiograph, and a tomographic image is reconstructed. Consequently, it is possible to obtain an image of a relatively stationary heart.

PTL 1 discloses a dose modulation method in which a relatively high dose of X-rays is applied in a specific heartbeat phase in which motion is reduced, and a low dose of X-rays is applied in other heartbeat phases, and thus an amount of radiation exposure is reduced while an image with phases other than the specific heartbeat phase can also be created.

In the method disclosed in PTL 1, an image with a phase in which imaging is performed in a low dose (hereinafter, referred to as a low dose phase image) has more deteriorated image quality than an image with a phase in which imaging is performed in a high dose. Thus, for example, in a case where images with all phases are reconstructed in order to observe an object over time, image quality varies due to a difference in an X-ray dose depending on the phases. In order to compensate for such a variation in image quality, an image quality improvement process may be performed on a low dose phase image. The image quality improvement process is a technique in which, for example, projection data is corrected, an image is reconstructed through successive approximation by using the corrected projection data, and thus a high image quality is achieved. In this image quality improvement process, an operator may designate an intensity level of the image quality improvement process in relation to the extent of improvement of image quality.

CITATION LIST

Patent Literature

PTL 1: JP-A-2007-117719

SUMMARY OF INVENTION

Technical Problem

However, in the related art, an intensity level of the image quality improvement process applied to the low dose phase image is judged and decided by the operator on the basis of experience or the like of the operator.

The present invention has been made in consideration of the above-described problems, and an object thereof is to provide an X-ray CT apparatus, an image processing device, and an image reconstruction method, capable of obtaining equivalent image quality in all sections when an image is reconstructed on the basis of projection data in which a low dose irradiation section and a high dose irradiation section are mixed.

Solution to Problem

In order to achieve the object, according to the present invention, there is provided an X-ray CT apparatus including an X-ray source that irradiates an object with X-rays; an X-ray detector that is disposed to oppose the X-ray source and detects X-rays having been transmitted through the object; a rotation board that mounts the X-ray source and the X-ray detector and is rotated around the object; an imaging control unit that performs imaging while modulating an irradiation X-ray dose on the basis of predetermined dose modulation data; a projection data generation unit that generates projection data on the basis of transmitted X-ray data detected by the X-ray detector; a storage unit that holds an image quality improvement table indicating image quality improvement effect amounts of a plurality of image quality improvement processes; a reference dose acquisition unit that sets a dose value corresponding to reference image quality as a reference dose; a reconstruction target dose acquisition unit that acquires an irradiation X-ray dose during imaging for image reconstruction target projection data, from the dose modulation data; an image quality improvement process selection unit that selects an image quality improvement process for obtaining the reference image quality from the image quality improvement table on the basis of a ratio between the reference dose and the irradiation X-ray dose acquired by the reconstruction target dose acquisition unit, and the image quality improvement effect amount; and a reconstruction processing unit that performs the image quality improvement process selected by the image quality improvement process selection unit on the image reconstruction target projection data, so as to reconstruct an image.

According to the present invention, there is provided an image processing device including a storage unit that stores projection data obtained through imaging using an X-ray CT apparatus, dose modulation data in the imaging, and an image quality improvement table indicating image quality improvement effect amounts of a plurality of image quality improvement processes; a goal image quality setting unit that sets an image quality index value used as goal image quality; a target image quality acquisition unit that acquires an image quality index value of an image quality improvement target image; an image quality improvement process selection unit that selects an image quality improvement process for obtaining the goal image quality from the image quality improvement table on the basis of a ratio between the image quality index value of the goal image quality and the image quality index value acquired by the target image quality acquisition unit, and the image quality improvement effect amount; and a reconstruction processing unit that performs the image quality improvement process selected by the image quality improvement process selection unit on projection data of the image quality improvement target image, so as to reconstruct an image.

According to the present invention, there is provided an image reconstruction method of causing an image processing device to execute a step of setting a dose value corresponding to reference image quality as a reference dose; a step of acquiring an irradiation X-ray dose during imaging for image reconstruction target projection data from the dose modulation data; a step of selecting an image quality improvement process for obtaining the reference image quality from an image quality improvement table indicating image quality improvement effect amounts of a plurality of image quality improvement processes, stored in a storage unit, on the basis of a ratio between the reference dose and the irradiation X-ray dose; and a step of performing the selected image quality improvement process on the image reconstruction target projection data, so as to reconstruct an image.

According to the present invention, there is provided an image reconstruction method of causing an image processing device to execute a step of setting an image quality index value used as goal image quality; a step of acquiring image quality of an image quality improvement target image; a step of selecting an image quality improvement process for obtaining the goal image quality from an image quality improvement table indicating image quality improvement effect amounts of a plurality of image quality improvement processes, stored in a storage unit, on the basis of a ratio between the goal image quality and the image quality of the image quality improvement target image; and a step of performing the selected image quality improvement process on projection data of the image quality improvement target image so as to reconstruct an image.

Advantageous Effects of Invention

According to the present invention, it is possible to provide an X-ray CT apparatus, an image processing device, and an image reconstruction method, capable of obtaining equivalent image quality in all sections when an image is reconstructed on the basis of projection data in which a low dose irradiation section and a high dose irradiation section are mixed.

BRIEF DESCRIPTION OF DRAWINGS

FIG. 15 is a flowchart illustrating procedures of imaging and reconstruction processes in a third embodiment of the present invention.

DESCRIPTION OF EMBODIMENTS

Hereinafter, embodiments of the present invention will be described in detail with reference to the drawings.

First Embodiment

First, with reference to FIG. 1, the entire configuration of an X-ray CT apparatus 1 will be described.

Figure 1:
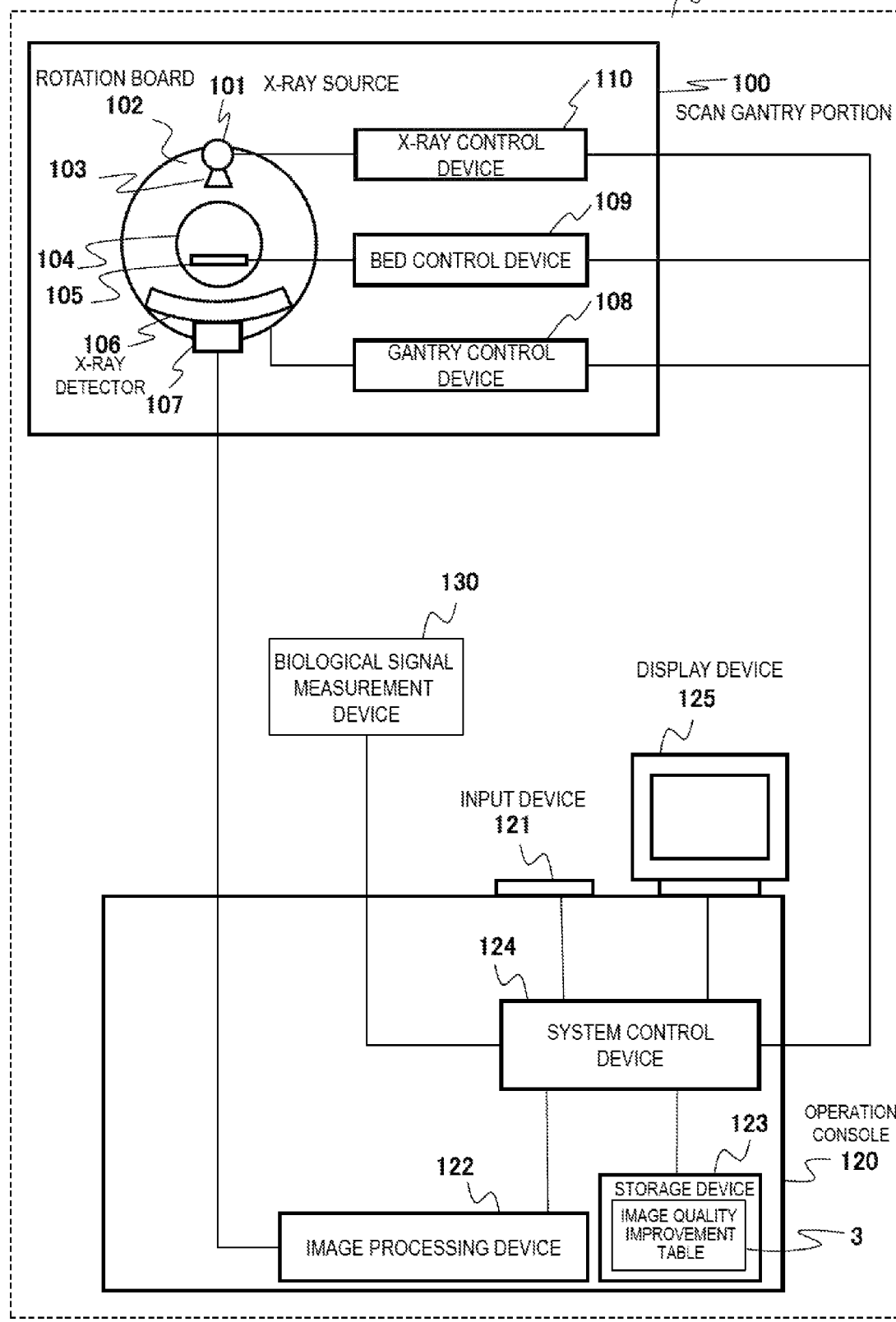
FIG. 1 is the entire configuration diagram of an X-ray CT apparatus 1.

As illustrated in FIG. 1, the X-ray CT apparatus 1 includes a scan gantry portion 100, a bed 105, an operation console 120, and a biological signal measurement device 130. The scan gantry portion 100 is a device which irradiates an object with X-rays, and detects X-rays having been transmitted through the object. The operation console 120 is a device which controls each constituent element of the scan gantry portion 100, and acquires transmitted X-ray data measured by the scan gantry portion 100 so as to generate an image. The bed 105 is a device on which the object is laid and is mounted and which carries the object into and out of an X-ray irradiation range of the scan gantry portion 100. The biological signal measurement device 130 is a device which measures data regarding motion of a living body, and is, for example, an electrocardiograph or a breathing gauge.

The scan gantry portion 100 includes an X-ray source 101, a rotation board 102, a collimator 103, an X-ray detector 106, a data collecting device 107, a gantry control device 108, a bed control device 109, and an X-ray control device 110.

The operation console 120 includes an input device 121, an image processing device 122, a storage device 123, a system control device 124, and a display device 125.

The rotation board 102 is provided with an opening 104, and the X-ray source 101 and the X-ray detector 106 are disposed to oppose each other with the opening 104 interposed therebetween. An object mounted on the bed 105 is inserted into the opening 104. The rotation board 102 is rotated around the object by a driving force which is transmitted from a rotation board driving device via a driving transmission system. The rotation board driving device is controlled by the gantry control device 108.

The X-ray source 101 is controlled by the X-ray control device 110 so as to apply X-rays with a predetermined intensity continuously or intermittently. The X-ray control device 110 controls an X-ray tube voltage applied to the X-ray source 101 and an X-ray tube current supplied thereto according to an X-ray tube voltage and an X-ray tube current determined by the system control device 124. The X-ray tube voltage and the X-ray tube current are determined depending on dose modulation data calculated by the system control device 124. The dose modulation data will be described later.

The collimator 103 is provided in an X-ray irradiation outlet of the X-ray source 101. The collimator 103 restricts an irradiation range of X-rays radiated from the X-ray source 101. For example, the X-rays are shaped a cone beam (a conical or pyramid beam) or the like. An aperture width of the collimator 103 is controlled by the system control device 124.

The X-rays, applied from the X-ray source 101, passing through the collimator 103, and transmitted through the object, are incident to the X-ray detector 106.

The X-ray detector 106 is a detector in which, for example, about 1000 X-ray detection element groups each constituted of a scintillator and a photodiode are arranged in a channel direction (rotation direction), and, for example, 1 to 320 X-ray detection element groups are arranged in a column direction (body axis direction). The X-ray detector 106 is disposed to oppose the X-ray source 101 via the object. The X-ray detector 106 detects a dose of X-rays applied from the X-ray source 101 and transmitted through the object, and outputs the dose to the data collecting device 107.

The data collecting device 107 collects an X-ray dose detected by each X-ray detection element of the X-ray detector 106, converts the X-ray dose into digital data, and sequentially outputs the digital data to the image processing device 122 as transmitted X-ray data.

The image processing device 122 acquires the transmitted X-ray data which is input from the data collecting device 107, and performs pre-processing such as logarithmic conversion and sensitivity correction on the data so as to generate projection data which is necessary in reconstruction. The image processing device 122 reconstructs an image such as a tomographic image by using the generated projection data. The system control device 124 stores image data reconstructed by the image processing device 122 in the storage device 123 and also displays the image data on the display device 125.

The system control device 124 is a computer provided with a central processing unit (CPU), a read only memory (ROM), a random access memory (RAM), and the like. The system control device 124 performs imaging and image reconstruction processes according to process procedures illustrated in FIG. 7 and the like. Details of the imaging and the image reconstruction processes will be described later.

The storage device 123 is a data recording device such as a hard disk, and stores in advance programs or data for realizing a function of the X-ray CT apparatus 1.

The storage device 123 stores an image quality improvement table 3.

Figure 2:
FIG. 2 illustrates an example of an image quality improvement table 3.

As illustrated in FIG. 2, the image quality improvement table 3 is a table indicating the image quality improvement effect amount for each of a plurality of image quality improvement processes with difference intensities. The image quality improvement effect amount is, for example, a value such as a noise reduction ratio for an image before and after the image quality improvement process is applied. The noise reduction ratio is expressed by a ratio between an image SD value of an original image before the image quality improvement process is applied and an image SD value after the image quality improvement process is applied. In the example illustrated in FIG. 2, in a case where an image quality improvement process at level 1 is applied, an image quality improvement effect (noise reduction effect) of 30% in terms of the image SD value is obtained compared with an original image before the image quality improvement process is applied.

In an image quality improvement process in a level of 2, an image quality improvement effect of 40% in terms of the image SD value is obtained compared with an original image before the image quality improvement process is applied, and, in an image quality improvement process in a level of 3, an image quality improvement effect of 50% in terms of the image SD value is obtained compared with an original image before the image quality improvement process is applied. In the present embodiment, an image quality evaluation index such as an image SD value is used as image quality, but image quality index values other than the image SD value may be used.

The image quality improvement table 3 illustrated in FIG. 2 shows a case where effect levels are five stages, but there may be a plurality of stages of levels according to aspects of the image quality improvement process. Procedures of creating the image quality improvement table 3 and a process of selecting an image quality improvement process will be described later in detail.

The display device 125 is constituted of a display device such as a liquid crystal panel or a CRT monitor, and a logic circuit for performing a display process in conjunction with the display device, and is connected to the system control device 124. The display device 125 displays an object image output from the image processing device 122, and various information treated by the system control device 124.

The input device 121 is constituted of, for example, a pointing device such as a keyboard or a mouse, ten keys, and various switch buttons, and outputs various instructions or information input by an operator, to the system control device 124. The operator operates the X-ray CT apparatus 1 in an interaction manner by using the display device 125 and the input device 121. The input device 121 may be a touch panel type input device which is integrally formed with a display screen of the display device 125.

The bed 105 is provided with a top plate on which the object is laid and is mounted, a vertical movement device, and a top plate driving device. Under the control of the bed control device 109, the top plate is vertically moved up and down, moved back and forth in the body axis direction, or moved left and right in a direction (leftward-and-rightward direction) which is perpendicular to the body axis and is parallel to a floor surface. During imaging, the bed control device 109 moves the top plate at a bed movement speed and in a movement direction, determined by the system control device 124.

The biological signal measurement device 130 is a device which measures data regarding physiological motion of the object. The motion of the object includes, for example, beating of the heart or motion of the lung due to breathing. In a case of measuring beating of the heart, for example, an electrocardiograph may be used as the biological signal measurement device 130. For example, in a case of measuring motion of the chest due to breathing, a respiration sensor or the like may be used as the biological signal measurement device 130. In the following description, an example in which beating of the heart is measured as motion information of the object will be described, but the present invention is also applicable to motions other than the beating of the heart.

Biological signals (motion information) measured by the biological signal measurement device 130 are sequentially transmitted to the system control device 124. The system control device 124 determines a modulation timing of an irradiation X-ray dose, or the irradiation X-ray dose, on the basis of the biological signals acquired from the biological signal measurement device 130, so as to calculate dose modulation data. The dose modulation data is, specifically, data indicating a modulation timing or a value of a tube current or a tube voltage.

Figure 3:
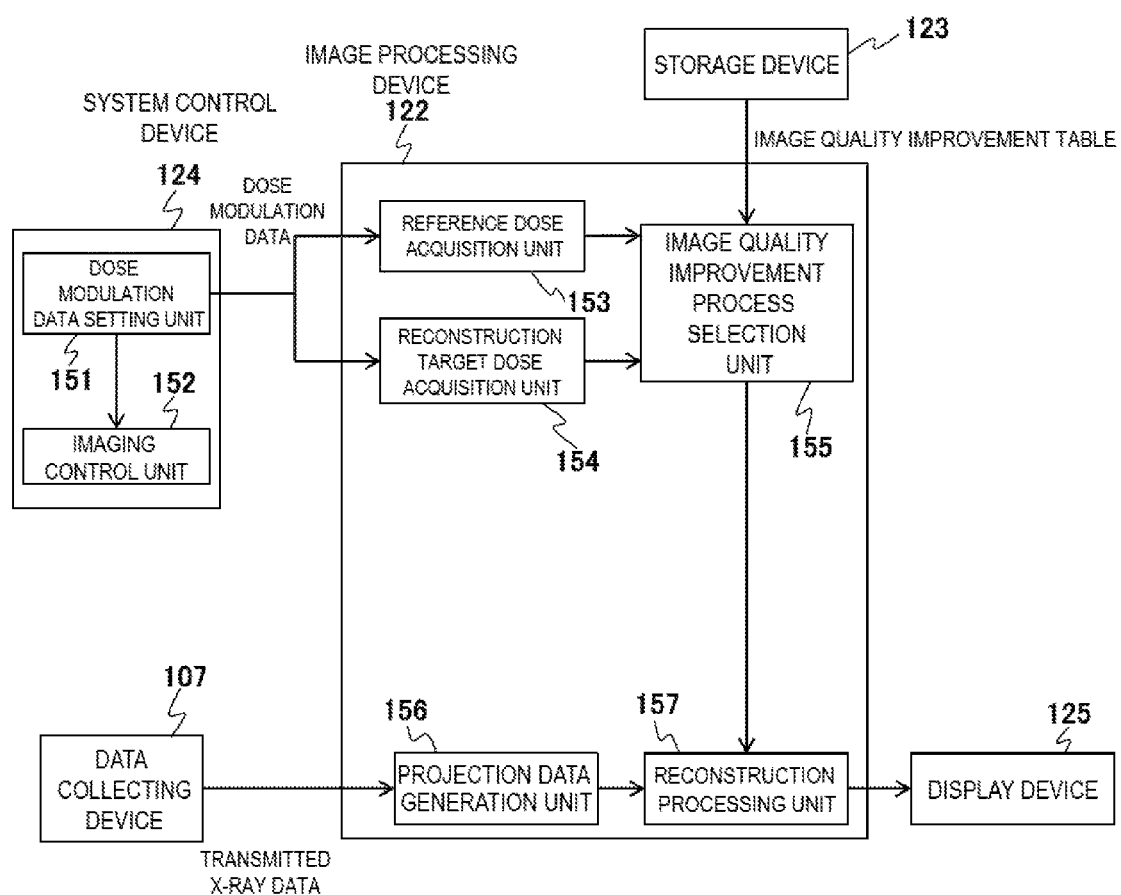
FIG. 3 is a functional configuration diagram related to an image quality improvement process in the X-ray CT apparatus 1 of the present invention.

Next, with reference to FIG. 3, functional configurations related to imaging and image reconstruction will be described.

The X-ray CT apparatus 1 of the present invention includes, as the functional configurations related to imaging and image reconstruction, a dose modulation data setting unit 151, an imaging control unit 152, a reference dose acquisition unit 153, a reconstruction target dose acquisition unit 154, an image quality improvement process selection unit 155, a projection data generation unit 156, and a reconstruction processing unit 157. From the viewpoint of processing load, preferably, the dose modulation data setting unit 151 and the imaging control unit 152 are provided in the system control device 124, and the reference dose acquisition unit 153, the reconstruction target dose acquisition unit 154, the image quality improvement process selection unit 155, the projection data generation unit 156, and the reconstruction processing unit 157 are provided in the image processing device 122. However, the reference dose acquisition unit 153, the reconstruction target dose acquisition unit 154, and the image quality improvement process selection unit 155 may be provided in the system control device 124.

Figure 4:
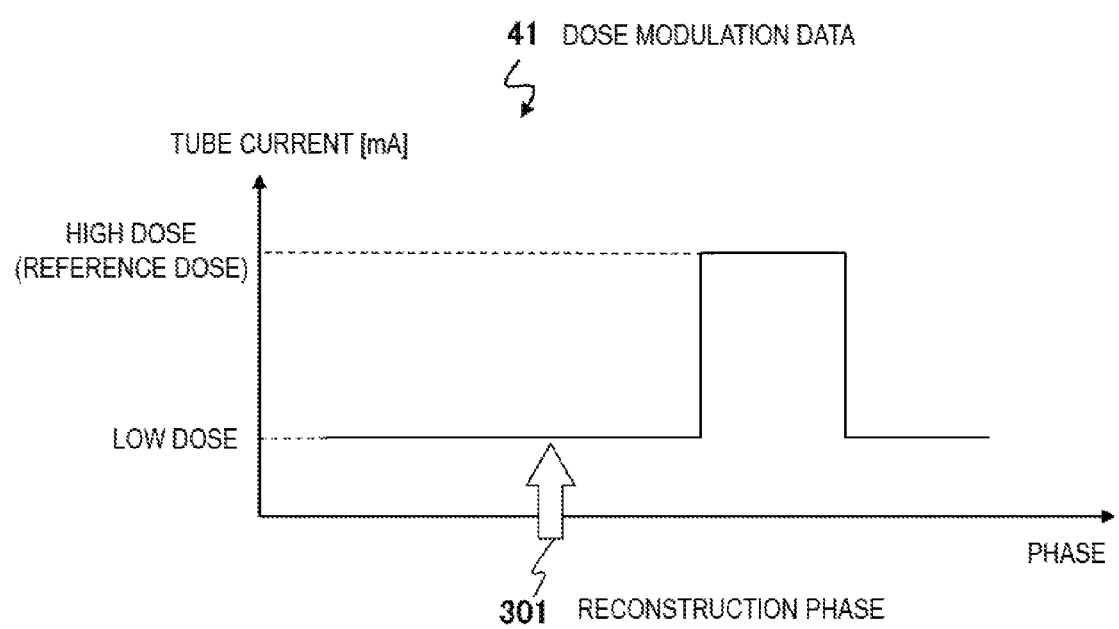
FIG. 4 illustrates examples of dose modulation data and a reference dose (in a case where a high dose value is used as a reference dose).

The dose modulation data setting unit 151 calculates dose modulation data for defining a modulation timing of an irradiation X-ray dose or an X-ray dose, and outputs the dose modulation data to the imaging control unit 152. For example, in a case of electrocardiographic synchronous imaging, the dose modulation data is calculated on the basis of a biological signal (electrocardiographic information) measured by the biological signal measurement device 130 (electrocardiograph). For example, as illustrated in FIG. 4, it is assumed that dose modulation data 41 is generated in which a high dose is used in a heartbeat phase in which motion is reduced, and a low dose is used in other heartbeat phases.

The imaging control unit 152 performs imaging while modulating an irradiation X-ray dose according to various imaging conditions including the dose modulation data set by the dose modulation data setting unit 151. Specifically, the imaging control unit 152 sends control signals to the X-ray control device 110, the gantry control device 108, and the bed control device 109 on the basis of the imaging conditions. The X-ray control device 110 controls power to be input to the X-ray source 101 on the basis of the dose modulation data which is input from the system control device 124. The gantry control device 108 controls the driving system of the rotation board 102 according to an imaging condition such as a rotation speed, so as to rotate the rotation board 102. The bed control device 109 positions the bed 105 to a predetermined imaging start position on the basis of an imaging range set as the imaging condition, and moves the top plate of the bed 105 at a predetermined speed on the basis of the imaging condition such as a bed speed (screw pitch) during imaging.

The reference dose acquisition unit 153 acquires a value of an irradiation X-ray dose (hereinafter, referred to as a reference dose) corresponding to reference image quality. The reference dose is set to a dose value corresponding to a "high dose" in the dose modulation data set by the dose modulation data setting unit 151, for example, as illustrated in FIG. 4. In this case, by performing a process which will be described later, image quality of a low dose phase image can be made to coincide with image quality of a high dose phase image. In the electrocardiographic synchronous imaging, a phase in which motion of the heart is reduced is likely to be included in a high dose irradiation section. Thus, a specific phase among heartbeat phases may be set as a phase corresponding to a reference dose.

Figure 5:
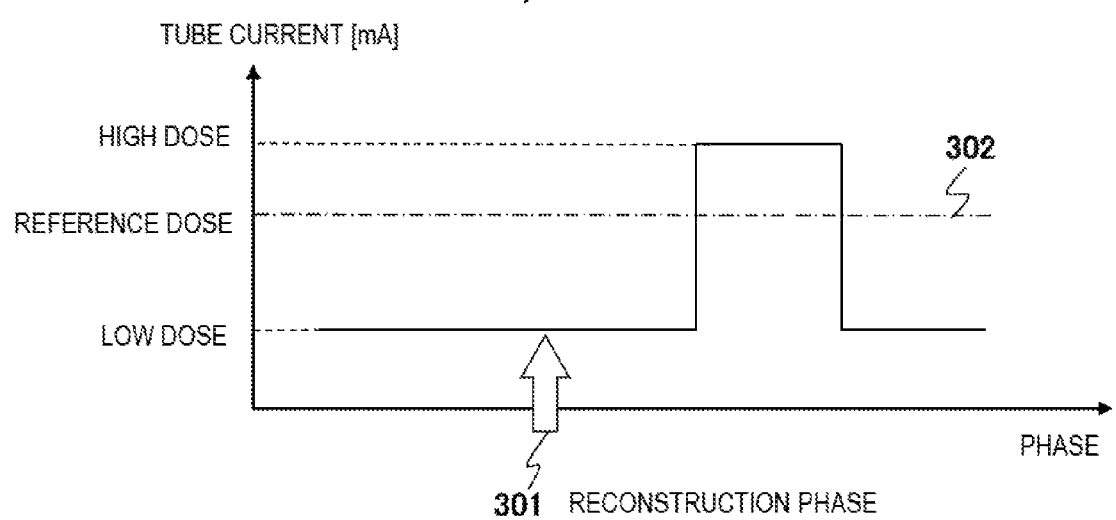
FIG. 5 illustrates other examples of dose modulation data and a reference dose (in a case where any dose value is used as a reference dose).

Alternatively, as illustrated in FIG. 5, regarding the reference dose, any dose designated by an operator may be used as a reference dose 302. Designation of a reference dose performed by the operator is assumed to be input via, for example, the input device 121. In a case where any dose value is used as a reference dose, the dose value is preferably a dose value between the high dose and the low dose in the dose modulation data 42. In this case, by performing a process which will be described later, image quality of a low dose phase image can be made close to image quality of a high dose phase image. For example, this is suitable for a case where image quality is desired to be improved while making much of image quality characteristics of an original image (an image before an image quality improvement process is applied) of a low dose phase image.

The reconstruction target dose acquisition unit 154 acquires, from the above-described dose modulation data, a dose during imaging for projection data which is an image reconstruction target. In the examples illustrated in FIGS. 4 and 5, a phase indicated by an arrow 301 is an image reconstruction target phase. The reconstruction target dose acquisition unit 154 acquires a value of an irradiation X-ray dose during imaging in a reconstruction target phase (projection data in a certain section) from the dose modulation data.

The image quality improvement process selection unit 155 selects an image quality improvement process for obtaining reference image quality from the image quality improvement table 3 on the basis of a ratio between the reference dose acquired by the reference dose acquisition unit 153 and the irradiation X-ray dose during imaging for the image reconstruction target projection data acquired by the reconstruction target dose acquisition unit 154, and the image quality improvement effect amount. The image quality improvement process selection unit 155 notifies the reconstruction processing unit 157 of the selected image quality improvement process. Details of selection of an optimal image quality improvement process in the image quality improvement process selection unit 155 will be described later.

The projection data generation unit 156 acquires the transmitted X-ray data which is detected by the X-ray detector 106 and is collected by the data collecting device 107, and performs pre-processing such as logarithmic conversion or sensitivity correction thereon so as to generate projection data which is necessary in image reconstruction. In the electrocardiographic synchronous imaging, projection data items obtained from angle directions corresponding to at least 180 degrees are combined with each other for each heartbeat phase so that a projection data set necessary in reconstruction is created.

The reconstruction processing unit 157 acquires reconstruction target projection data from the projection data generation unit 156. The reconstruction processing unit 157 applies the image quality improvement process selected by the image quality improvement process selection unit 155 to the acquired projection data, so as to reconstruct a tomographic image of the object. The tomographic image reconstructed by the reconstruction processing unit 157 is stored in the storage device 123 and is also sent to the system control device 124 so as to be displayed on the display device 125.

Next, a description will be made of procedures of creating the image quality improvement table 3 and selection of an image quality improvement process using the image quality improvement table 3.

Figure 6:
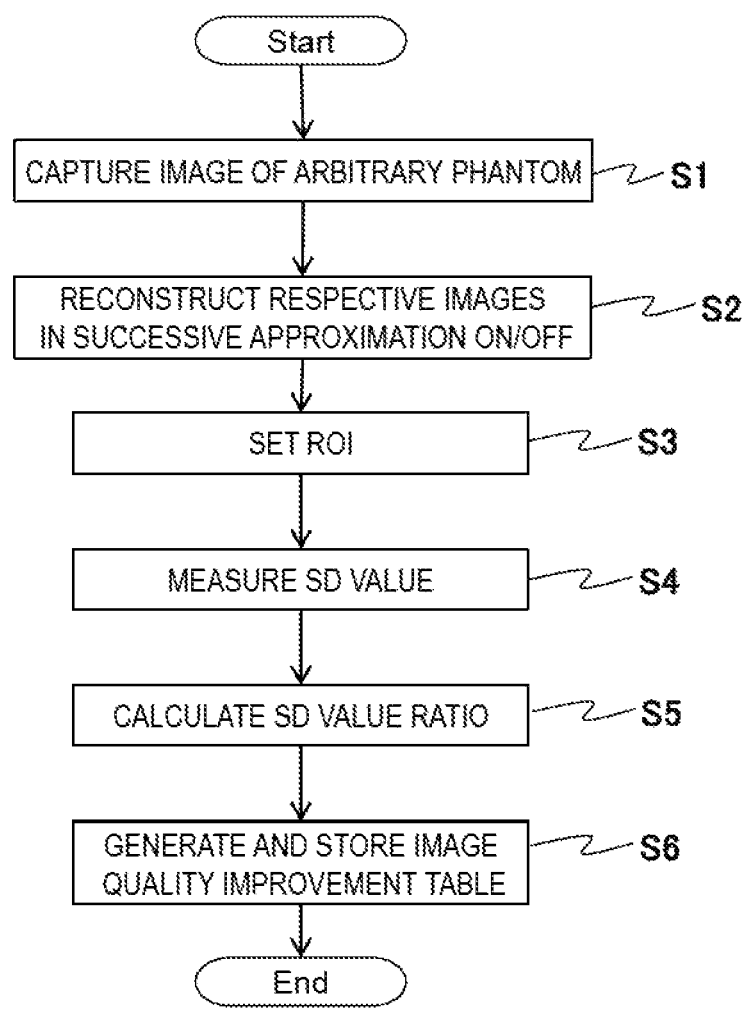
FIG. 6 is a flowchart illustrating procedures of a process of creating the image quality improvement table 3.

The image quality improvement table 3 illustrated in FIG. 2 is created in advance, for example, according to procedures illustrated in FIG. 6 and is stored in the storage device 123.

An image quality improvement process preferably employs a successive approximation reconstruction process. In the successive approximate reconstruction process, the image quality improvement effect amount differs depending on a level. Therefore, the image quality improvement effect amount for each level is calculated by imaging any object such as a phantom, and thus the image quality improvement table 3 is created.

First, the X-ray CT apparatus 1 images any phantom so as to obtain projection data (step S1). Next, the image processing device 122 reconstructs an image having undergone a successive approximation process (successive approximation ON) and an original image not having undergone the successive approximation process (successive approximation OFF) with respect to the projection data obtained in step S1 (step S2). There are a plurality of stages of intensity levels (Level 1 to Level 5 in FIG. 2) in the successive approximation process, and the successive approximation process is performed on the same measured data in each intensity level, and thus each image is reconstructed. Reconstruction conditions other than the intensity level of the successive approximation process are equalized. The original image (successive approximation process OFF) is reconstructed according to an analytical method such as a filtered back projection (FBP) method.

The image processing device 122 sets a region of interest (ROI) in the same portions of the respective images reconstructed in step S2 (step S3). The image processing device 122 measures an image SD value in the ROI of each image set in step S3 (step S4). The reason why the ROI is set in each image is that an image SD value partially differs even in a single tomographic image.

The image processing device 122 obtains a ratio between the image SD values in each ROI in the original image in which the successive approximation process is in an OFF state and the image in which the successive approximation process is in an ON state, and sets the obtained ratio as the image quality improvement effect amount (step S55). The process in step S5 is performed on the successive approximation process (image quality improvement process) in each level, and each image quality improvement effect amount (image SD value ratio) is obtained for the image quality improvement process in each level so that a table is created. The image processing device 122 stores the table created in step S6 in the storage device 123 as the image quality improvement table 3 (step S6).

In a case where a successive approximation reconstruction process in which the FBP method and an iterative process are combined is employed as an image quality improvement process, it is expected that an SD improvement effect differs depending on a reconstruction filter used for the FBP method. Thus, preferably, the image quality improvement effect amount of the image quality improvement process is measured for all reconstruction filter conditions, and thus a table is created.

Next, a description will be made of selection of the image quality improvement process using the image quality improvement table 3.

It is known that a dose value (mAs value) and an image SD value which is an index indicating image quality have a relationship of the following Expression (1).

[Expression 1]

$$\text{Image } SD \text{ value} \propto 1/\sqrt{(mAs \text{ value})} \qquad (1)$$

Therefore, a ratio between a reference dose (tube current) and a dose (tube current) of reconstruction target imaging data and a necessary image noise reduction ratio may have a relationship expressed as in the following Equation (2).

[Expression 2]

$$Y=1-X^2 \qquad (2)$$

Here, X indicates (the dose of reconstruction target projection data)/(the reference dose).

Y indicates an image SD value ratio (the image quality improvement effect amount defined in the image quality improvement table 3).

The image SD value ratio Y is, that is, an image noise reduction ratio.

In dose modulation control, since a scanning speed does not vary, and an mAs value is known, first, the image quality improvement process selection unit 155 obtains a tube current ratio X (dose ratio), and obtains a ratio Y between image SD values of a reference dose original image and a reconstruction target original image by using the obtained tube current ratio (dose ratio) and the above Equation (2). The image quality improvement process selection unit 155 selects an image quality improvement process (a level thereof) corresponding to the ratio Y between the image SD values from the image quality improvement table 3. In a case where there is no image quality improvement process in a level for accurate improvement, an image quality improvement process in the closest level is selected from the image quality improvement table 3.

For example, in a case where a tube current value used as a reference dose is 600 mA, and a tube current in a reconstruction target phase is 300 mA, an image quality improvement process in which the image quality improvement effect amount (image SD value ratio=noise reduction ratio) is 75% is selected.

For example, in a case where a tube current value used as a reference dose is 600 mA, and a tube current in a reconstruction target phase is 500 mA, an image quality improvement process in which the image quality improvement effect amount is 30% is selected.

In a case where a difference between a reference dose and a reconstruction target dose is considerably great and thus is not satisfied by the image quality improvement effect amount defined in the image quality improvement table 3, it is preferable to notify the operator that the operator prompts reexamination of a dose. For example, it is preferable to display a message for prompting a decrease of a reference dose or an increase of a low dose value in the dose modulation data, on the display device 125.

Next, with reference to FIGS. 7 to 9, an operation of the X-ray CT apparatus 1 will be described.

Figure 7:
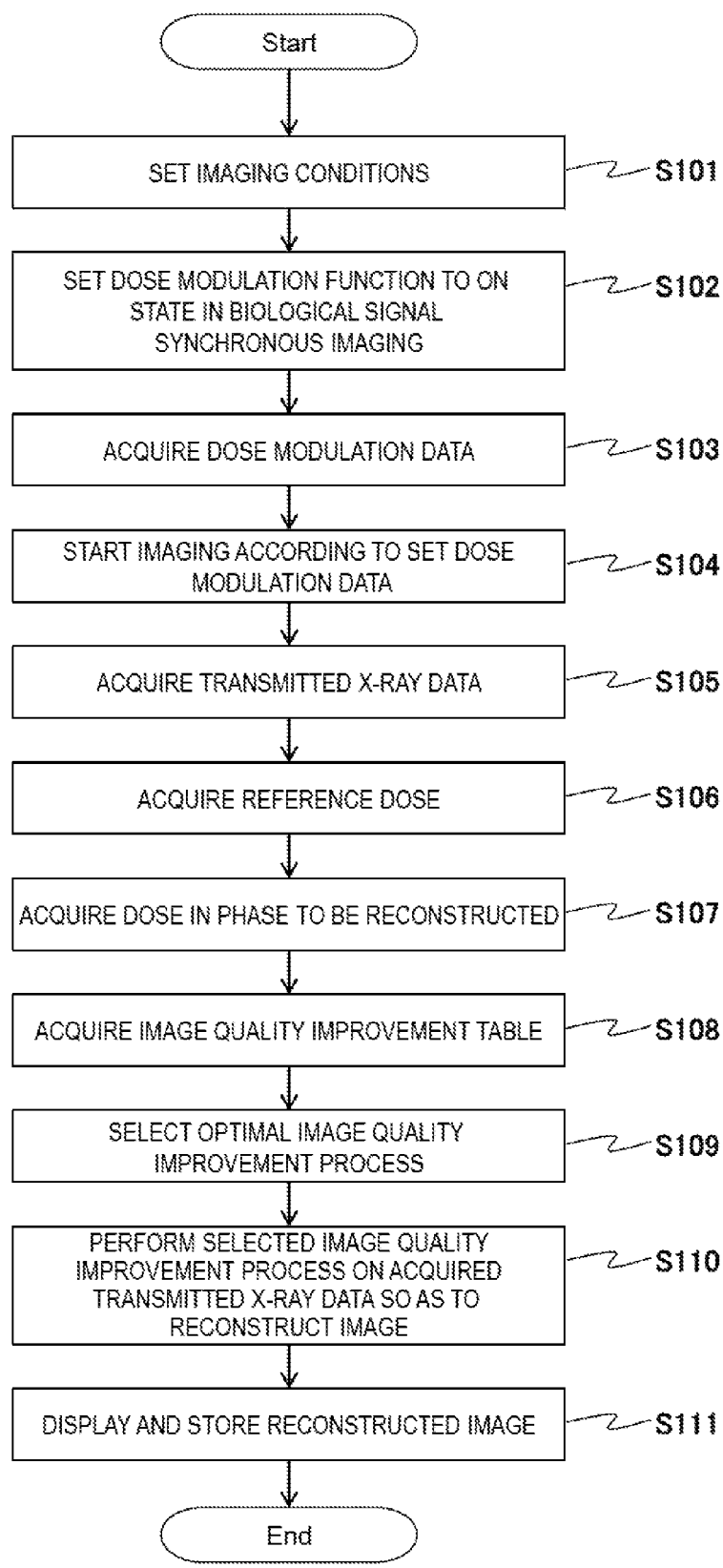
FIG. 7 is a flowchart illustrating procedures of imaging and reconstruction processes in the X-ray CT apparatus 1 of the present invention.

The system control device 124 of the X-ray CT apparatus 1 performs imaging and image reconstruction processes according to procedures shown in a flowchart of FIG. 7. In other words, the system control device 124 reads a program and data regarding the imaging and image reconstruction processes from the storage device 123, and performs the processes on the basis of the program and the data.

In the X-ray CT apparatus 1, first, the operator sets imaging conditions (step S101), and sets a dose modulation function in biological signal synchronous imaging to an ON state (step S102). If the dose modulation function is set to an ON state, the system control device 124 calculates dose modulation data in which a modulation timing or a value of an X-ray tube current or an X-ray tube voltage is adjusted so as to synchronize with the biological signal. If the dose modulation data is acquired (step S103), the system control device 124 sends an imaging starting signal to each constituent element of the scan gantry portion 100. The scan gantry portion 100 performs imaging while modulating a tube current or a tube voltage on the basis of the dose modulation data acquired in step S103 (step S104).

If the imaging is started, the system control device 124 sends control signals to the X-ray control device 110, the gantry control device 108, and the bed control device 109 on the basis of the imaging conditions. The X-ray control device 110 controls power to be input to the X-ray source 101 on the basis of the control signal which is input from the system control device 124. The gantry control device 108 controls the driving system of the rotation board 102 according to the imaging condition such as a rotation speed, so as to rotate the rotation board 102. The bed control device 109 positions the bed 105 to a predetermined imaging start position on the basis of an imaging range, and moves the top plate of the bed 105 on the basis of the imaging condition such as a bed speed (screw pitch) during imaging. In the above-described manner, X-ray irradiation from the X-ray source 101 and measurement of transmitted X-ray data in the X-ray detector 106 are repeatedly performed along with rotation of the rotation board 102.

The data collecting device 107 collects transmitted X-ray data measured by the X-ray detector 106 in various angles (views) of the periphery of the object, and sends the transmitted X-ray data to the image processing device 122. The image processing device 122 acquires the transmitted X-ray data from the data collecting device 107 (step S105).

The image processing device 122 acquires a dose value (reference dose) used as a reference of image quality from the dose modulation data acquired in step S103 (step S106). For example, a high dose value is acquired.

The image processing device 122 acquires a value of a dose in a phase to be reconstructed from the dose modulation data acquired in step S103 (step S107). For example, if a phase to be reconstructed is included in a low dose irradiation section, a value of the low dose is acquired.

The image processing device 122 acquires the image quality improvement table 3 from the storage device 123 (step S108).

The image processing device 122 determines an optimal image quality improvement process so that quality of an image in the phase to be reconstructed is close to image quality in a case where irradiation is performed in the reference dose, on the basis of a ratio between the value of the reference dose acquired in step S106 and the value of the dose in the phase to be reconstructed acquired in step S107 (step S109). Here, the optimal image quality improvement process is an image quality improvement process for compensating for image quality before improvement up to image quality obtained in a case where imaging is performed in an accurate reference dose. For example, in a case where a low dose value is reduced by 50% relative to a high dose value, an image quality improvement process for achieving an improvement effect corresponding to a dose ratio of 50% is selected by referring to the image quality improvement table 3 illustrated in FIG. 2. Consequently, an image quality of a low dose phase image can be improved to the same extent as an image quality of a high dose phase image. If there is no image quality improvement process for achieving an accurately corresponding improvement effect, an image quality improvement process which allows image quality closest to the reference to be obtained among image quality improvement processes which can be performed, may be selected from the image quality improvement table 3.

Figure 8:
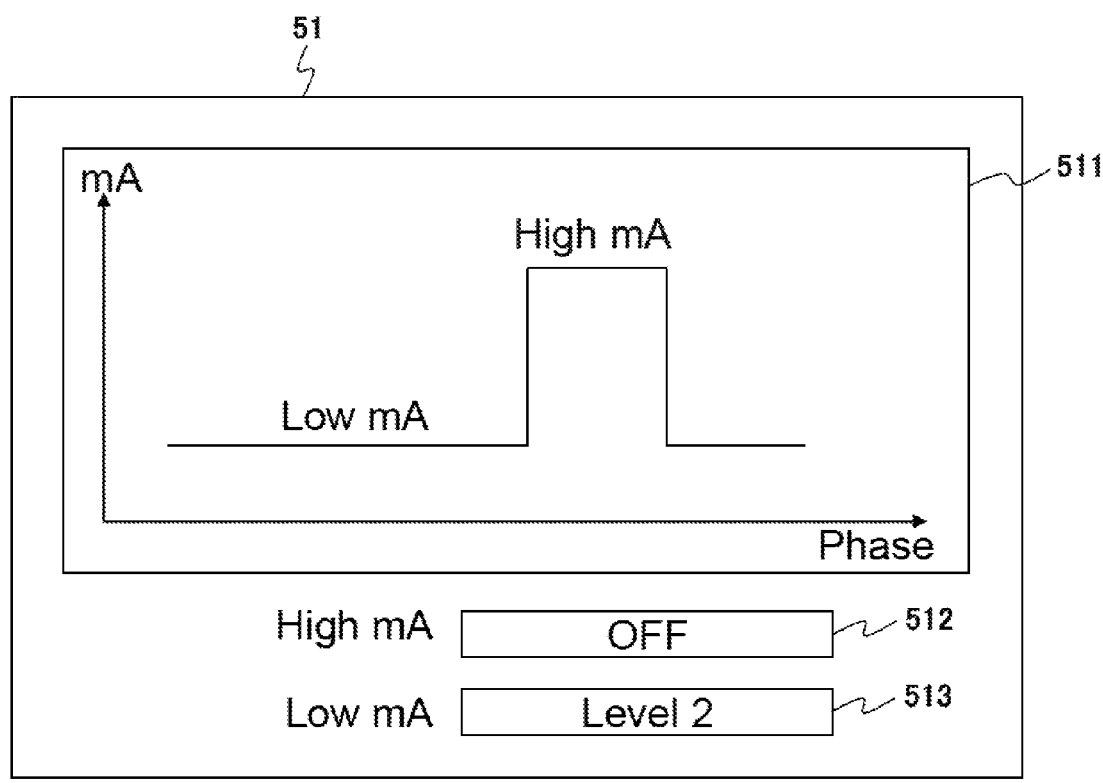
FIG. 8 illustrates a display example of an image quality improvement process selected by an image quality improvement process selection unit 155.
Figure 9:
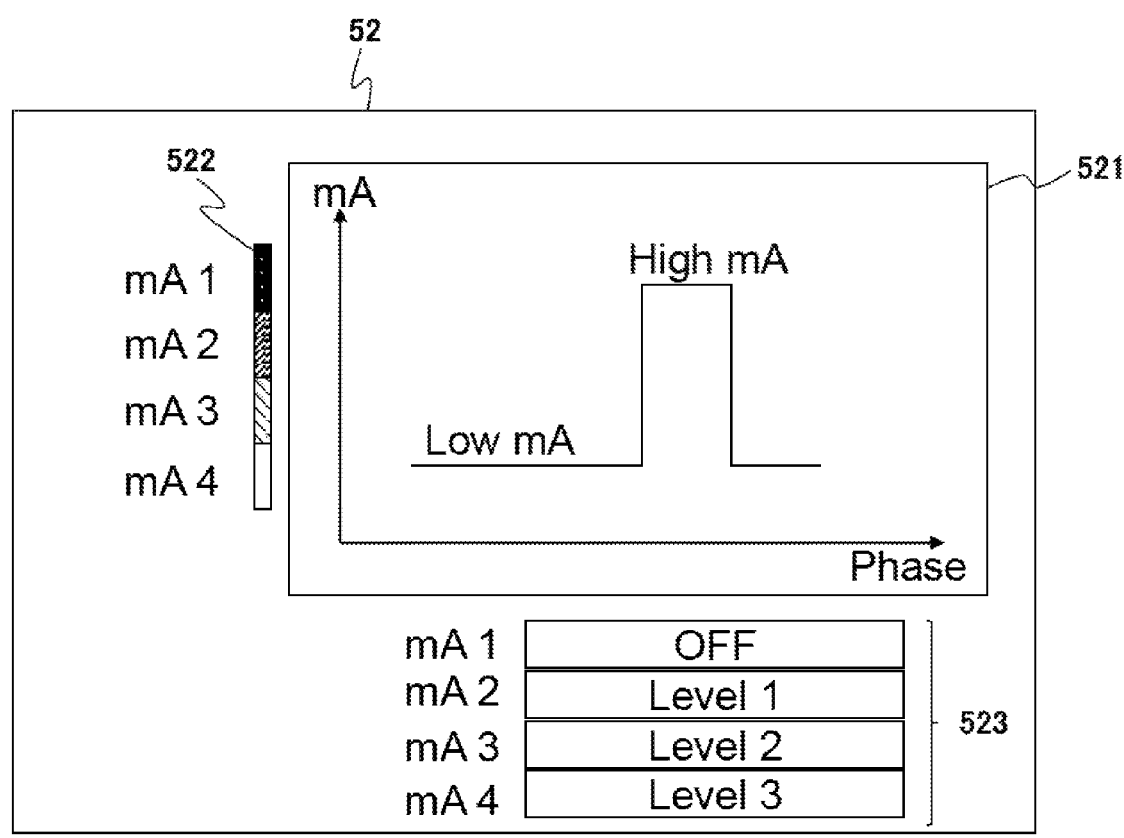
FIG. 9 illustrates a screen display example using a guide 522 indicating a relationship between a reference dose and the selected image quality improvement process.

In step S109, the system control device 124 may display a display screen 51 or 52 illustrated in FIG. 8 or 9 on the display device 125.

The display screen 51 illustrated in FIG. 8 has a dose modulation data display column 511 in which the dose modulation data is displayed in a graph form, and process display columns 512 and 513 indicating an image quality improvement process applied to projection data obtained through imaging using each dose value.

A graph of dose modulation data displayed in the dose modulation data display column 511 is a graph indicating the dose modulation data acquired in step S103. A longitudinal axis of the graph indicating the dose modulation data expresses, for example, a tube current value, and a transverse axis thereof expresses a phase.

The process display column 512 displays an image quality improvement process applied to a high dose phase (High mA). In a case where a high dose value is used as a reference dose, as illustrated in FIG. 8, an image quality improvement process for a high dose phase is in an "OFF" state. The process display column 513 displays an image quality improvement process applied to a low dose phase (Low mA). The example illustrated in FIG. 8 shows that an image quality improvement process in "Level 2" is selected.

The display screen 52 illustrated in FIG. 9 has a dose modulation data display column 521 in which the dose modulation data is displayed in a graph form, a guide 522 indicating in advance image quality improvement processes which are selected depending on a dose value difference from a reference dose (mA1), and a process display column 523 indicating levels of image quality improvement processes selected depending on a dose value difference. The guide 522 is displayed along a longitudinal axis of the graph indicating the dose modulation data. The display screen 52 illustrated in FIG. 9 is suitable in a case where dose modulation is performed not in two stages such as a high dose and a low dose but in multiple stages.

In the display screen 51 or 52 illustrated in FIG. 8 or 9, the operator may set or change an image quality improvement process. In this case, preferably, as a guide, optimal image quality improvement processes are presented in advance, or the type of selectable image quality improvement process is restricted on the basis of a reference dose and a dose value difference in a reconstruction phase.

FIG. 7 is referred to again for description.

The image processing device 122 applies the image quality improvement process selected in step S109 to the phase to be reconstructed so as to reconstruct an image (step S110).

The system control device 124 stores the reconstructed image in the storage device 123 and also displays the reconstructed image on the display device 125 (step S111), and finishes a series of processes.

As described above, the X-ray CT apparatus 1 of the present invention holds the image quality improvement table 3 indicating levels of image quality improvement effects for a plurality of image quality improvement processes. The X-ray CT apparatus 1 performs imaging while modulating an X-ray irradiation amount on the basis of predetermined dose modulation data. The image processing device 122 acquires a reference dose used as a reference of image quality, acquires an irradiation X-ray dose during imaging for image reconstruction target projection data from the dose modulation data, determines an optimal image quality improvement process for obtaining image quality used as a reference by referring to the image quality improvement table 3 on the basis of a ratio between the dose values, and performs the determined image quality improvement process on the reconstruction target projection data.

Consequently, when an image is reconstructed by using projection data in which a low dose irradiation section and a high dose irradiation section are mixed, an image quality improvement process which leads to the appropriate image quality improvement effect amount is applied to projection data obtained through imaging in a low dose, and thus it is possible to obtain an image having the same extent of image quality as image quality obtained through imaging in a reference dose. Since the optimal image quality improvement process is determined by the X-ray CT apparatus 1, the optimal image quality improvement process can be performed without depending on an operator's experiences and the like.

Preferably, the dose modulation data is determined on the basis of data regarding motion of a living body measured by the biological signal measurement device. Consequently, for example, in the electrocardiographic synchronous imaging in which imaging is performed by modulating a dose according to motion of the heart or the like, image quality variations between a high does phase and a low dose phase can be suppressed, and thus it becomes easier to view each image when checking motion of the heart throughout all heartbeat phases. The same process is applicable not only to motion of the heart but also motion due to breathing.

Particularly, in a case where the dose modulation data is data for instructing high dose irradiation in a specific phase and low dose irradiation in other phases according to a periodical motion of the object, if a reference dose is set as a dose (high dose) in the specific phase, it is possible to obtain image quality which is equivalent to image quality in the high dose phase throughout all phases while maintaining a reduction effect of an amount of radiation exposure due to the dose modulation.

The reference dose may be any dose between a high dose and a low dose. For example, in a case where an image quality improvement process in a high level is performed, image quality is improved, but processing time may be lengthened. However, in a case where processing time is prioritized, an image quality improvement process in an appropriate level can be selected. An image close to an original image is preferably used depending on a purpose of diagnosis. In this case, an image quality improvement process corresponding to an operator's need can be performed.

If complex setting operations or the like for improving image quality are omitted, and dose modulation imaging is set to an "ON" state before starting imaging, process procedures of reconstructing an image having undergone an optimal image quality improvement process are executed in interlocking with the operation, and thus an operator can obtain an image with improved image quality through a simple operation.

In the process described in the first embodiment, when an optimal image quality improvement process is selected, a dose ratio (tube current ratio Y) is calculated on the basis of a reference dose value and a reconstruction target dose value, the image quality improvement effect amount X is obtained by using Equation (2), and the optimal image quality improvement process is selected from the image quality improvement table 3. However, instead of the reference dose or the like, goal image quality (reference image quality) may be set by using, for example, an image quality index value such as an image SD value. An image quality improvement process may be selected on the basis of a ratio between the set goal image quality and image quality (SD value) corresponding to a dose of reconstruction target projection data.

Second Embodiment

Next, with reference to FIGS. 10 to 12, a second embodiment of the present invention will be described.

There is a limit in the image quality improvement effect amount of an image quality improvement process, and thus there may be a case where improvement up to reference image quality cannot be achieved by using any image quality improvement process depending on a relationship between a reference dose and an irradiation dose during imaging for obtaining reconstruction target projection data. Therefore, in the second embodiment, a system control device 124a of the X-ray CT apparatus 1 obtains a lower limit value of a low dose value in advance before imaging by referring to the image quality improvement table 3 stored in the storage device 123, so as to limit a dose modulation range.

A hardware configuration of the X-ray CT apparatus 1 of the second embodiment is the same as that in FIG. 1. In the following description, the same reference numerals are given the same constituent elements, and repeated description will be omitted.

Figure 10:
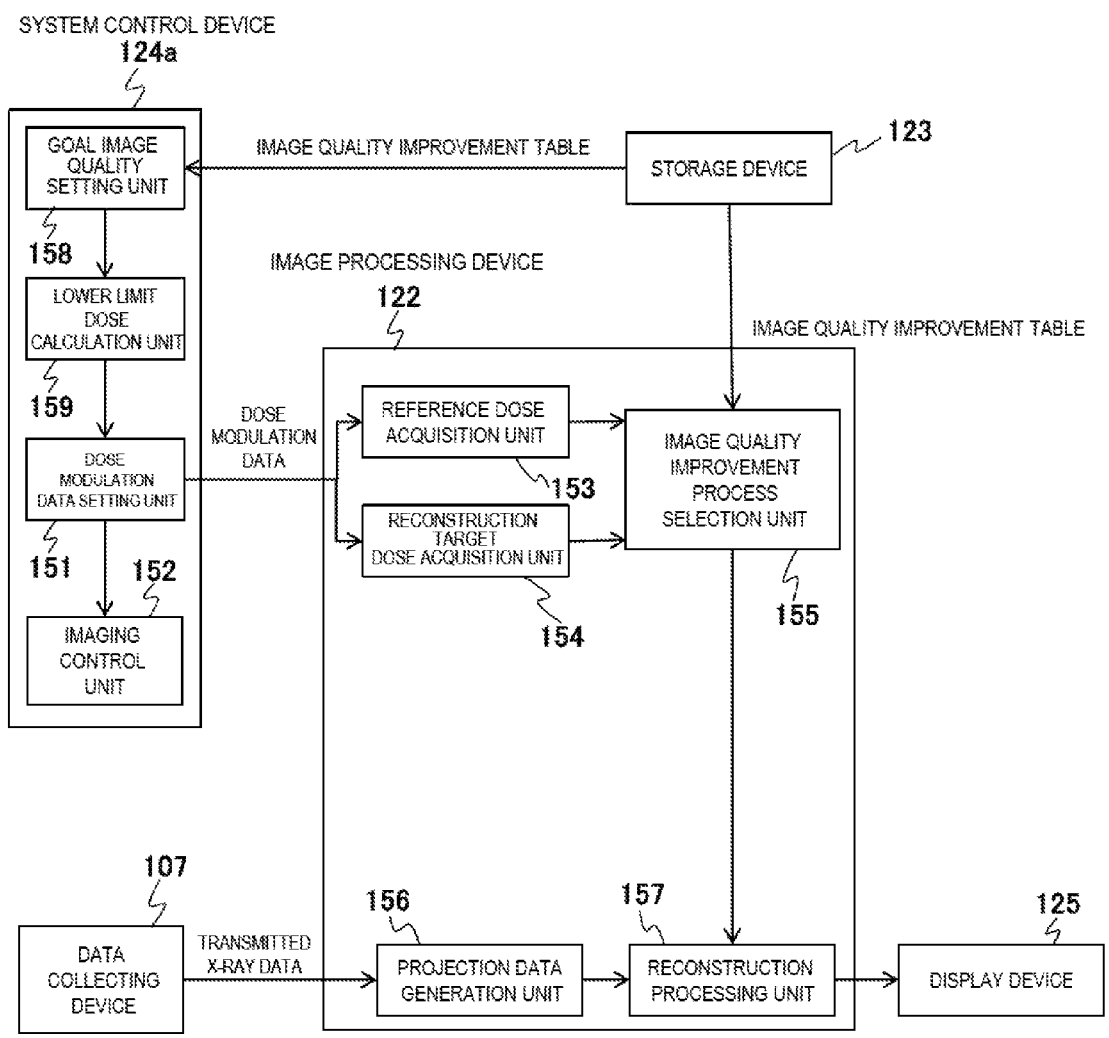
FIG. 10 is a functional configuration diagram in a second embodiment of the present invention.

FIG. 10 illustrates a functional configuration related to imaging and reconstruction processes according to the second embodiment. In the second embodiment, the system control device 124a includes a goal image quality setting unit 158 and a lower limit dose calculation unit 159 in addition to the functional configuration (the dose modulation data setting unit 151 and the imaging control unit 152 in FIG. 3) of the system control device 124 of the first embodiment. The image processing device 122 has the same functional configuration as that of the image processing device 122 of the first embodiment.

The goal image quality setting unit 158 arbitrarily sets image quality corresponding to the operator's goal. For example, image quality obtained by performing irradiation with a predetermined high dose value is used as goal image quality. The goal image quality may be designated by an image quality target value, and may be designated by a dose value which is necessary in order to achieve the goal image quality.

The lower limit dose calculation unit 159 acquires the image quality improvement table 3 from the storage device 123, and calculates a lower limit value of an irradiation X-ray dose on the basis of the largest image quality improvement effect amount among the image quality improvement effect amounts defined in the image quality improvement table 3 and the goal image quality (a dose value for achieving the goal image quality) set by the goal image quality setting unit 158. The lower limit value may be obtained by dividing the dose value for achieving the goal image quality by the image quality improvement effect amount. The lower limit dose calculation unit 159 notifies the dose modulation data setting unit 151 of the calculated lower limit value of the irradiation X-ray dose.

The dose modulation data setting unit 151 sets dose modulation data so that a lower limit value of the irradiation X-ray dose is not smaller than the lower limit value calculated by the lower limit dose calculation unit 159.

As mentioned above, it is possible to perform the same imaging and image quality improvement processes as those in the first embodiment by using dose modulation data which is set by taking into consideration the largest image quality improvement effect amount.

In this case, the reference dose acquisition unit 153 acquires a dose value for achieving goal image quality set by the operator in the goal image quality setting unit 158, as a reference dose.

Figure 11:
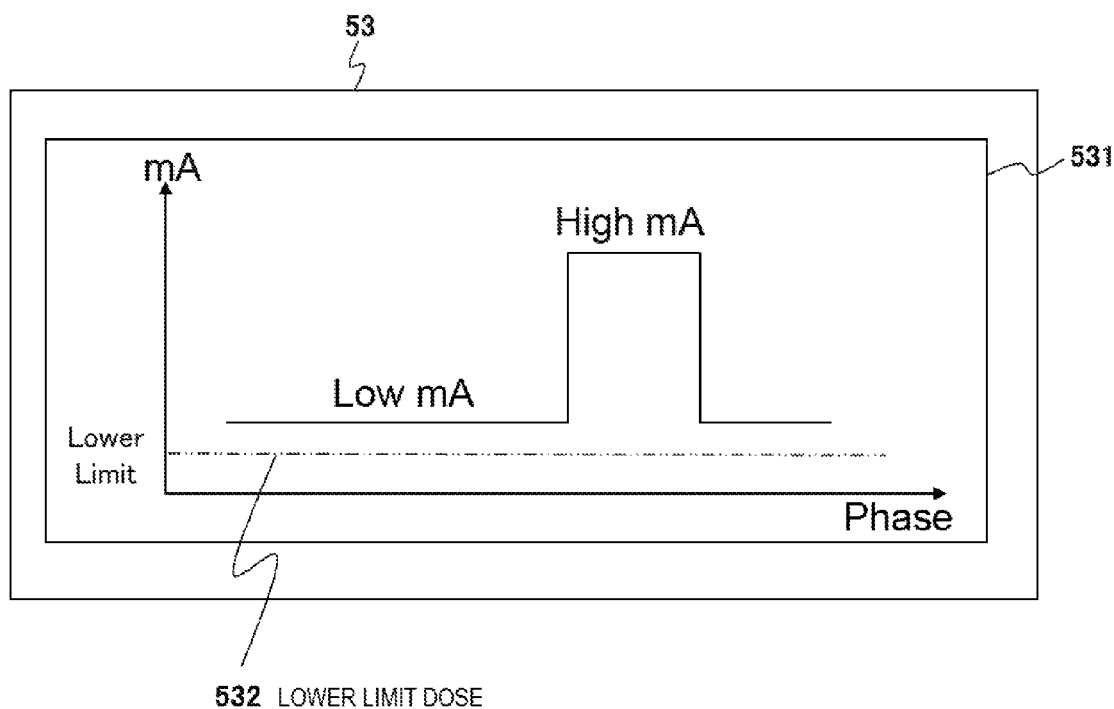
FIG. 11 is a diagram for explaining calculation of a lower limit dose 532.

The system control device 124a preferably displays, for example, a dose modulation data display screen 53 as illustrated in FIG. 11, on the display device 125. In this case, the system control device 124a preferably provides a display 532 indicating the lower limit value of the dose calculated by the lower limit dose calculation unit 159 in a graph 531 indicating the dose modulation data.

Figure 12:
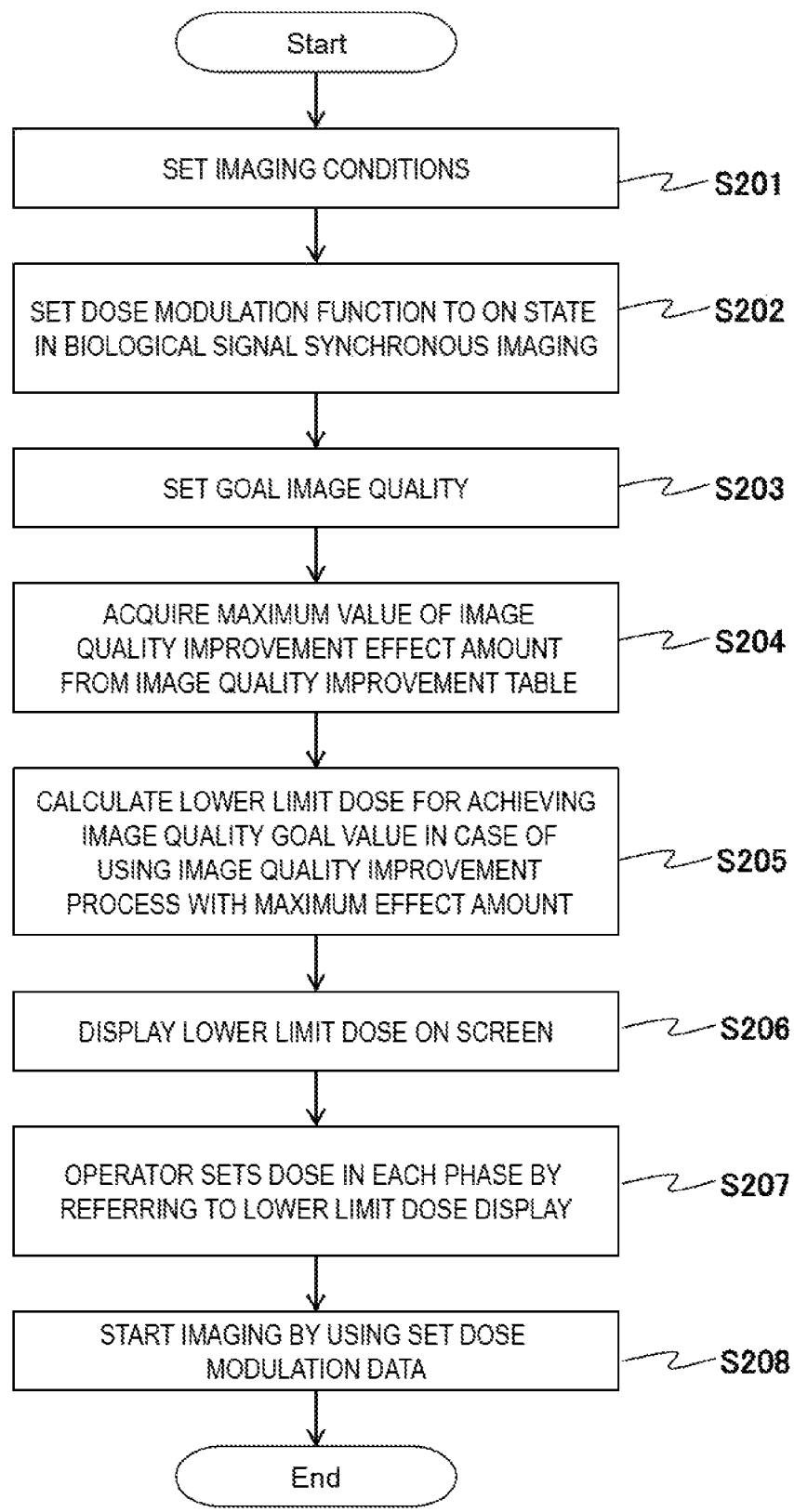
FIG. 12 is a flowchart illustrating procedures of imaging and reconstruction processes in the second embodiment of the present invention.

With reference to FIG. 12, an operation of the X-ray CT apparatus 1 of the second embodiment will be described.

In the second embodiment, the system control device 124a of the X-ray CT apparatus 1 performs imaging and image reconstruction processes according to procedures shown in a flowchart of FIG. 12. In other words, the system control device 124a reads a program and data regarding the imaging and image reconstruction processes from the storage device 123, and performs the processes on the basis of the program and the data.

First, the operator sets imaging conditions (step S201), and sets a dose modulation function in biological signal synchronous imaging to an ON state (step S202). If the dose modulation function is set to an ON state, the system control device 124a calculates dose modulation data in which a modulation timing or a tube current amount of an X-ray tube current is adjusted so as to synchronize with biological signal.

The system control device 124a receives goal image quality set by the operator (step S203). In step S203, if a goal image quality index value or a target dose value is input via the input device 121, the system control device 124a sets goal image quality on the basis of the input value.

Next, the system control device 124a acquires the image quality improvement table 3 from the storage device 123, and acquires the largest image quality improvement effect amount from among the image quality improvement effect amounts defined in the image quality improvement table 3 (step S204). The system control device 124a calculates a lower limit value (lower limit dose) of an irradiation X-ray dose on the basis of the largest image quality improvement effect amount acquired in step S204 and the goal image quality (or the dose value for achieving the goal image quality) set in step S203 (step S205). The lower limit dose may be obtained by dividing the high dose value by the improvement effect amount. The system control device 124a displays the calculated lower limit dose on the display device 125 along with the dose modulation data. For example, a lower limit dose 532 is displayed on the dose modulation data display screen 53 as illustrated in FIG. 11 (step S206).

The operator may adjust a dose in each phase while referring to the lower limit dose 532 displayed on the dose modulation data display screen 53 (step S207). In step S207, the system control device 124a restricts an adjustment operation performed by the operator so that a dose value is not smaller than the lower limit dose value. The dose value in each phase set through the adjustment operation performed by the operator is set as dose modulation data, and imaging is started (step S208).

The subsequent processes are the same as the processes in steps S105 to S111 in the first embodiment. However, in the reference dose acquisition process in step S106, a dose value necessary in order to achieve the goal image quality set in step S203 is acquired as the reference dose.

If an image quality improvement process applied to a phase to be reconstructed is selected, an image having undergone the image quality improvement process is reconstructed, and the reconstructed image is displayed on the display device 125 and is stored in the storage device 123, through the processes in steps S105 to S111, the system control device 124a finishes a series of imaging and reconstruction processes.

As described above, the X-ray CT apparatus 1 of the second embodiment calculates a lower limit dose for achieving an image quality goal value in a case where an image quality improvement process exhibiting the largest image quality improvement effect amount defined in the image quality improvement table 3 is applied, and sets dose modulation data so that a dose value is not smaller than the lower limit dose.

Therefore, it is possible to prevent imaging in a low dose which cannot achieve an effect of the image quality improvement process. It is also possible to achieve goal image quality set by the operator by using projection data obtained through imaging in a low dose.

Third Embodiment

Next, with reference to FIGS. 13 to 15, a third embodiment of the present invention will be described.

In the first embodiment, procedures of an image quality improvement process in the image reconstruction process during imaging of the object have been exemplified, but an image quality improvement process of the present invention is also applicable to projection data which is obtained in advance through imaging and is stored in the storage device 123. In the first embodiment, reference image quality is determined by selecting a dose value or a phase, but, actually, reconstructed images in respective phases are displayed as moving images or are enumerated and are displayed, and reference (goal) image quality is designated from the images.

In the third embodiment, a description can be made of application of an image quality improvement process to stored projection data and setting of goal image quality.

A hardware configuration of the X-ray CT apparatus 1 of the third embodiment is the same as that in FIG. 1. In the following description, the same reference numerals are given the same constituent elements, and repeated description will be omitted.

Figure 13:
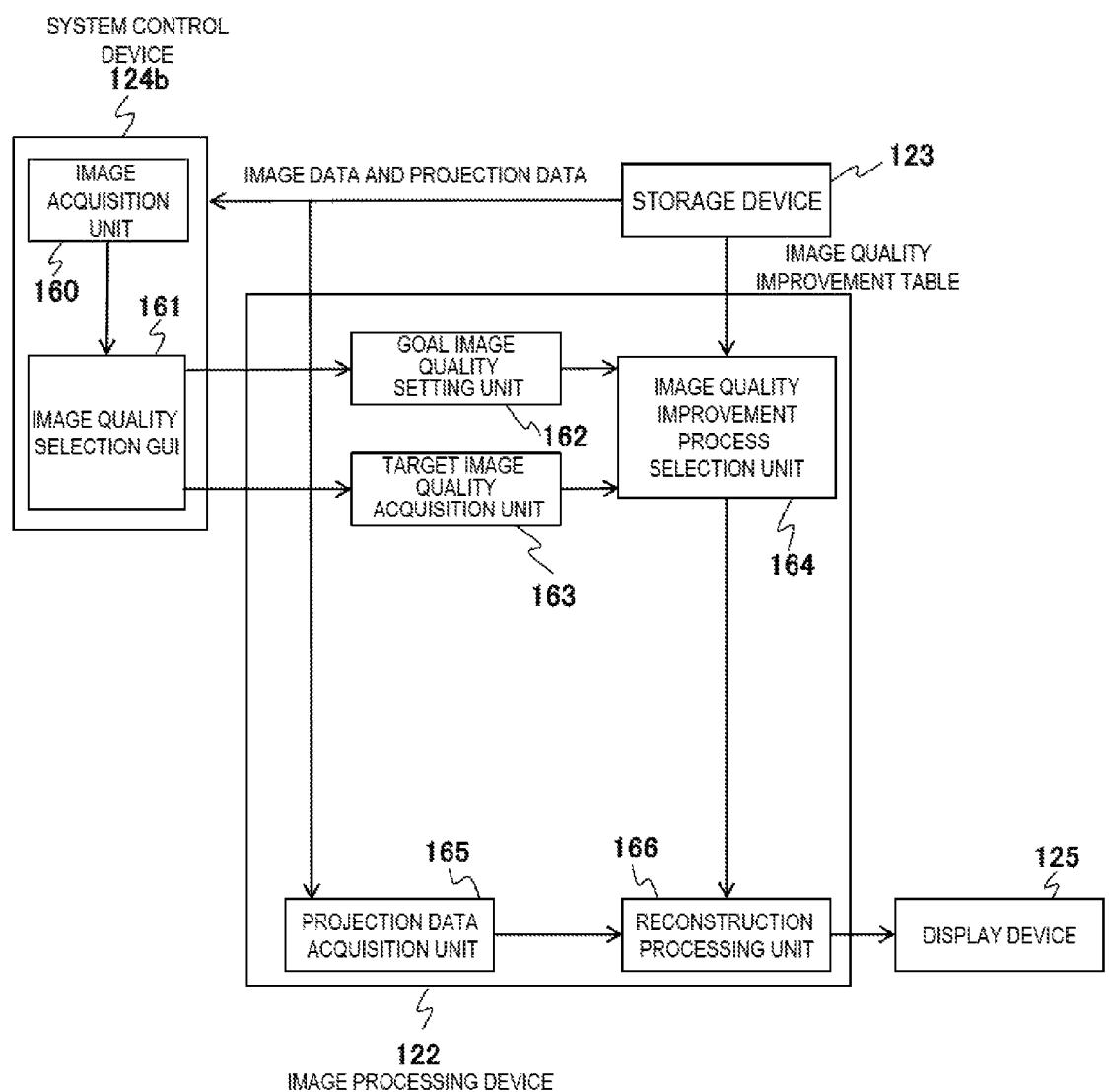
FIG. 13 is a functional configuration diagram in a third embodiment of the present invention.

FIG. 13 illustrates a functional configuration related to imaging and reconstruction processes according to the third embodiment. In the third embodiment, a system control device 124b includes an image acquisition unit 160 and an image quality selection graphical user interface (GUI) 161. An image processing device 122 includes a goal image quality setting unit 162, a target image quality acquisition unit 163, an image quality improvement process selection unit 164, a projection data acquisition unit 165, and a reconstruction processing unit 166.

The image acquisition unit 160 acquires image data which is a candidate of image quality improvement from the storage device 123. For example, images in all heartbeat phases obtained through electrocardiographic synchronous imaging are acquired.

Figure 14:
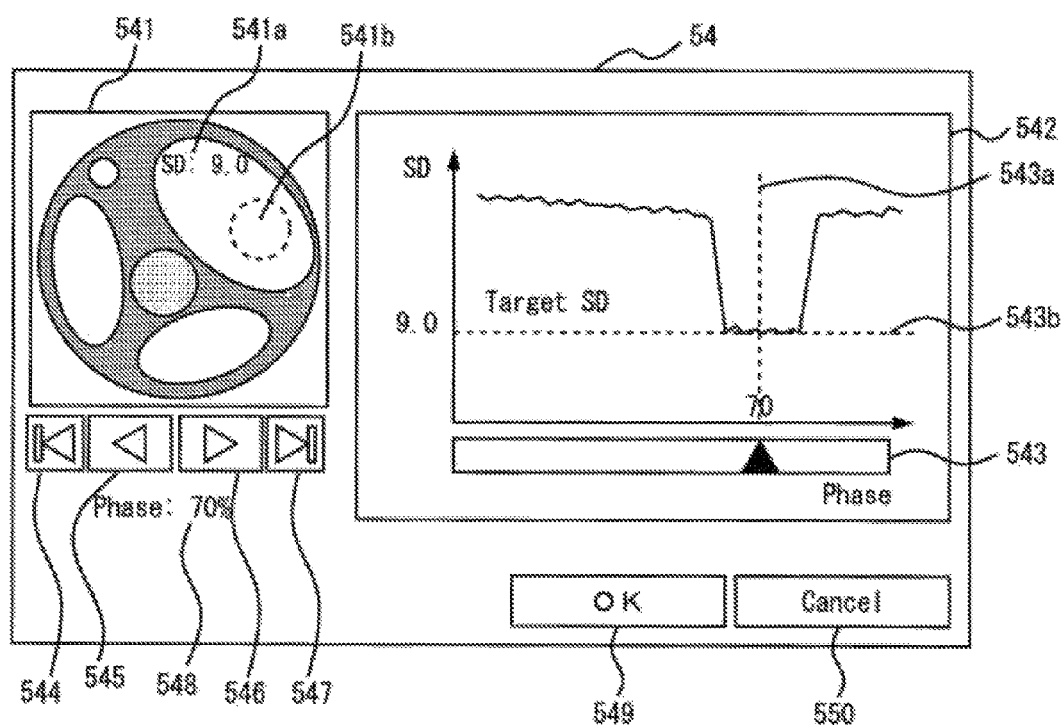
FIG. 14 illustrates an example of an image quality selection GUI 161 (operation screen 54).

The image quality selection GUI 161 (operation unit) is a GUI for setting goal image quality, and includes an operation screen 54 as illustrated in FIG. 14, for example.

The operation screen 54 of the image quality selection GUI 161 illustrated in FIG. 14 is provided with a tomographic image display column 541 in which a series of tomographic images are displayed frame by frame in a time series; an image quality graph display column 542 in which an image quality graph indicating a relationship between an image quality index value (for example, an image SD value) and a phase for an image displayed in the tomographic image display column 541; a goal image quality selection bar 543 for designating goal image quality in the image quality graph; a fast rewind button 544; a rewind button 545; a forward button 546; a fast forward button 547; a selected phase display 548; an OK button 549; a cancel button 550; and the like.

A mark 541b indicating an image quality evaluation region (ROI) designated by the operator, and an image quality index value 541a (for example, an image SD value) in the ROI 541b are displayed on the tomographic image displayed in the tomographic image display column 541.

A transverse axis of the image quality graph displayed in the image quality graph display column 542 expresses a phase, and a longitudinal axis thereof expresses an image quality index value such as an image SD value. The image quality index value of the image quality graph is an actually calculated image quality index value for the image quality evaluation region (ROI 541b) designated by the operator in the tomographic image display column 541.

The goal image quality selection bar 543 is provided along the transverse axis (phase axis) of the image quality graph, and a phase is designated by horizontally moving a position of a slider (a triangular mark in FIG. 14) provided along the bar. A tomographic image in the designated phase is displayed in the tomographic image display column 541. Preferably, an auxiliary line 543a indicating a slider position, and an auxiliary line 543b indicating an image quality index value in a phase at the slider position are displayed along with the goal image quality selection bar 543. FIG. 14 illustrates that the slider of the goal image quality selection bar 543 is moved to a position of the phase "70"%, and an image quality index value in the phase "70"% is a value of "9.0".

A tomographic image displayed in the tomographic image display column 541 is selected by the operator operating the fast rewind button 544, the rewind button 545, the forward button 546, and the fast forward button 547. Positions of the auxiliary lines 543a and 543b in the image quality graph display column 542 are changed in accordance with the tomographic image displayed in the tomographic image display column 541.

The operation screen 54 of the image quality selection GUI 161 illustrated in FIG. 14 is only an example, and an operation unit for image quality designation may be provided in a form separate from this example, and may be provided in a different display form.

The goal image quality setting unit 162 acquires the image quality index value of the tomographic image designated by the image quality selection GUI 161, and sets the value as goal image quality.

The target image quality acquisition unit 163 acquires image quality of an image quality improvement target image.

The image quality improvement process selection unit 164 selects an image quality improvement process necessary for obtaining the goal image quality from the image quality improvement table 3 on the basis of a ratio between the goal image quality set by the goal image quality setting unit 162 and the image quality of the image quality improvement target image acquired by the target image quality acquisition unit 163. As described above, since, in the image quality improvement table 3 illustrated in FIG. 2, an image SD value ratio is used as the image quality improvement effect amount, a ratio between the goal image quality set by the goal image quality setting unit 162 and the image quality of the image quality improvement target image acquired by the target image quality acquisition unit 163 is obtained, and an image quality improvement process corresponding to the obtained ratio is selected from the image quality improvement table 3.

The projection data acquisition unit 165 acquires projection data of the image quality improvement target image from the storage device 123.

The reconstruction processing unit 166 performs the image quality improvement process selected by the image quality improvement process selection unit 164 on the projection data of the image quality improvement target image so as to reconstruct an image.

Next, with reference to FIG. 15, a description will be made of an operation of the X-ray CT apparatus 1 in the third embodiment.

In the third embodiment, the system control device 124b of the X-ray CT apparatus 1 performs an image reconstruction process according to procedures of a flowchart illustrated in FIG. 15. In other words, the system control device 124b reads a program and data regarding the image reconstruction process from the storage device 123, and performs the process on the basis of the program and the data.

The operator selects reconstruction target series (tomographic image group) from among images stored in the storage device 123 (step S301). The system control device 124b reads the series of images in respective phases selected in step S301 from the storage device 123 so as to enumerate and display the images or to display the images as moving images (step S302). In step S302, the series of images are displayed, for example, in a form of forwarding or rewinding each frame as in the tomographic image display column 541 of the operation screen 54 illustrated in FIG. 14.

Frames of an image or a moving image having goal image quality are selected by the operator operating the fast rewind button 544, the rewind button 545, the forward button 546, the fast forward button 547, or the goal image quality selection bar 543 of the operation screen 54 (step S303). If the OK button 549 is pressed, the system control device 124b calculates image quality (image SD value) of the image selected in step S303 so as to hold the image quality in a RAM or the like as the goal image quality, and notifies the image processing device 122 of the goal image quality (step S304).

In step S304, preferably, an image quality evaluation region (ROI) is set on the image, and an image SD value in the image quality evaluation region (ROI) is obtained. The obtained image SD value is preferably displayed on the operation screen 54.

If a phase to be reconstructed is selected through the operator's operation (step S305), the image processing device 122 calls the image quality improvement table 3 from the storage device 123 (step S306).

The image processing device 122 acquires a dose in the selected phase (step S307).

An optimal image quality improvement process is determined on the basis of the image quality goal value determined in step S304 and the dose acquired in step S307 by referring to the image quality improvement table 3 (step S308).

The image processing device 122 applies the image quality improvement process selected in step S308 to the reconstruction target projection data, so as to reconstruct an image (step S309). The system control device 124b stores the reconstructed images in the storage device 123 and also displays the image on the display device 125 (step S310), and finishes a series of processes.

As described above, the image reconstruction process (including an image quality improvement process) according to the present invention is also applicable to projection data which is obtained in advance through imaging and is stored in the storage device 123. The operator may determine reference image quality by designating a predetermined image quality index value. In this case, a plurality of images which are already reconstructed and are stored in the storage device 123 are displayed, and goal image quality is set by the operator designating a desired image from among the images. Thus, it is possible to set goal image quality through an intuitive operation.

As mentioned above, the preferred embodiments of the X-ray CT apparatus according to the present invention have been described, but the present invention is not limited to the above embodiments. It is obvious that a person skilled in the art can conceive of various modifications or alterations within the scope of the technical spirit disclosed in the present application, and it is understood that they naturally fall within the technical scope of the present invention.

REFERENCE SIGNS LIST

1 X-RAY CT APPARATUS
100 SCAN GANTRY PORTION
101 X-RAY SOURCE
102 ROTATION BOARD
106 X-RAY DETECTOR
120 OPERATION CONSOLE
121 INPUT DEVICE
122 IMAGE PROCESSING DEVICE
123 STORAGE DEVICE
124 SYSTEM CONTROL DEVICE
125 DISPLAY DEVICE
130 BIOLOGICAL SIGNAL MEASUREMENT DEVICE
151 DOSE MODULATION DATA SETTING UNIT
152 IMAGING CONTROL UNIT
153 REFERENCE DOSE ACQUISITION UNIT
155 IMAGE QUALITY IMPROVEMENT PROCESS SELECTION UNIT
156 PROJECTION DATA GENERATION UNIT
157 RECONSTRUCTION PROCESSING UNIT
154 RECONSTRUCTION TARGET DOSE ACQUISITION UNIT
158 GOAL IMAGE QUALITY SETTING UNIT
159 LOWER LIMIT DOSE CALCULATION UNIT
161 IMAGE QUALITY SELECTION GUI (OPERATION UNIT)
54 OPERATION SCREEN
3 IMAGE QUALITY IMPROVEMENT TABLE

The invention claimed is:

1. An X-ray CT apparatus comprising:
an X-ray source that irradiates an object with X-rays;
an X-ray detector that is disposed to oppose the X-ray source and detects X-rays having been transmitted through the object;
a rotation board that is mounted with the X-ray source and the X-ray detector and is rotated around the object;
an imaging control unit that performs imaging while modulating an irradiation X-ray dose on the basis of predetermined dose modulation data;
a projection data generation unit that generates projection data on the basis of transmitted X-ray data detected by the X-ray detector;
a storage unit that holds an image quality improvement table indicating image quality improvement effect amounts of a plurality of image quality improvement processes;
a reference dose acquisition unit that sets a dose value corresponding to reference image quality as a reference dose;
a reconstruction target dose acquisition unit that acquires an irradiation X-ray dose during imaging for image reconstruction target projection data, from the dose modulation data;
an image quality improvement process selection unit that selects an image quality improvement process for obtaining the reference image quality from the image quality improvement table on the basis of a ratio between the reference dose and the irradiation X-ray dose acquired by the reconstruction target dose acquisition unit, and the image quality improvement effect amount; and
a reconstruction processing unit that performs the image quality improvement process selected by the image quality improvement process selection unit on the image reconstruction target projection data, so as to reconstruct an image.

2. The X-ray CT apparatus according to claim 1, wherein, in a case where the dose modulation data is determined according to periodical motion of the object, and is data for giving an instruction for a high dose of X-ray irradiation in a specific phase in the periodical motion, and an instruction for a low dose of X-ray irradiation lower than the high dose in other phases, and
wherein the reference dose acquisition unit acquires a dose value in the specific phase from the dose modulation data as the reference dose.

3. The X-ray CT apparatus according to claim 1, wherein, in a case where the dose modulation data is determined according to periodical motion of the object, and is data for giving an instruction for a high dose of X-ray irradiation in a specific phase in the periodical motion, and an instruction for a low dose of X-ray irradiation lower than the high dose in other phases,
the X-ray CT apparatus further includes a reference dose designation unit that designates any dose value between the high dose and the low dose as the reference dose, and
wherein the reference dose acquisition unit acquires the reference dose designated by the reference dose designation unit.

4. The X-ray CT apparatus according to claim 2, further comprising:
a biological signal measurement device that measures data regarding motion of a living body, wherein the dose modulation data is determined on the basis of motion of a living body measured by the biological signal measurement device.

5. The X-ray CT apparatus according to claim 1, further comprising:
a display unit that displays the image quality improvement process selected by the image quality improvement process selection unit along with the dose modulation data.

6. The X-ray CT apparatus according to claim 1, further comprising:
a lower limit dose calculation unit that acquires the image quality improvement table from the storage unit, and calculates a lower limit value of an irradiation X-ray dose on the basis of the maximum value of the image quality improvement effect amount defined in the image quality improvement table and the reference dose acquired by the reference dose acquisition unit; and
a dose modulation data setting unit that sets the dose modulation data so that the irradiation X-ray dose is not less than the lower limit value calculated by the lower limit dose calculation unit.

7. An image processing device comprising:
a storage unit that stores projection data obtained through imaging using an X-ray CT apparatus, dose modulation data in the imaging, and an image quality improvement table indicating image quality improvement effect amounts of a plurality of image quality improvement processes;
a goal image quality setting unit that sets an image quality index value used as goal image quality;
a target image quality acquisition unit that acquires an image quality index value of an image quality improvement target image;
an image quality improvement process selection unit that selects an image quality improvement process for obtaining the goal image quality from the image quality improvement table on the basis of a ratio between the image quality index value of the goal image quality and the image quality index value acquired by the target image quality acquisition unit, and the image quality improvement effect amount; and
a reconstruction processing unit that performs the image quality improvement process selected by the image quality improvement process selection unit on projection data of the image quality improvement target image, so as to reconstruct an image.

8. The image processing device according to claim 7, further comprising:
an operation unit that displays images which are generated by using projection data stored in the storage unit and on which the image quality improvement process is not performed, in a selectable manner,
wherein the goal image quality setting unit sets the goal image quality by selecting an image in the operation unit.

9. An image reconstruction method of causing an image processing device to execute:
a step of setting a dose value corresponding to reference image quality as a reference dose;
a step of acquiring an irradiation X-ray dose during imaging for image reconstruction target projection data from dose modulation data;
a step of selecting an image quality improvement process for obtaining the reference image quality from an image quality improvement table indicating image quality improvement effect amounts of a plurality of image quality improvement processes, stored in a storage unit, on the basis of a ratio between the reference dose and the irradiation X-ray dose; and
a step of performing the selected image quality improvement process on the image reconstruction target projection data, so as to reconstruct an image.

\* \* \* \* \*